US007006678B2

(12) United States Patent
Sawada

(10) Patent No.: US 7,006,678 B2
(45) Date of Patent: Feb. 28, 2006

(54) IMAGE INFORMATION PROCESSING SYSTEM

(75) Inventor: Hirofumi Sawada, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 582 days.

(21) Appl. No.: 09/991,922

(22) Filed: Nov. 26, 2001

(65) Prior Publication Data
US 2002/0122579 A1     Sep. 5, 2002

(30) Foreign Application Priority Data
Nov. 24, 2000   (JP)   .............................. 2000-357177

(51) Int. Cl.
*G06K 9/00*   (2006.01)
(52) U.S. Cl. .................. 382/132; 382/149; 378/28
(58) Field of Classification Search ................ 382/128, 382/129, 130, 131, 132, 133, 134, 149, 168, 382/181, 189, 214, 221, 252, 254, 268, 274, 382/295, 305, 306; 378/2, 21, 28, 62; 348/180; 377/28; 705/2, 3; 345/530; 600/425; 250/590, 250/584, 582, 581
See application file for complete search history.

(56) References Cited
U.S. PATENT DOCUMENTS 4,900,927 A * 2/1990 Kimura et al. .............. 250/590
5,335,172 A * 8/1994 Matsumoto et al. ........ 250/582
5,592,374 A * 1/1997 Fellegara et al. ............... 705/3
5,623,560 A * 4/1997 Nakajima et al. ........... 382/295
5,807,256 A * 9/1998 Taguchi et al. ............. 600/425
5,832,055 A * 11/1998 Dewaele ...................... 378/62
5,841,148 A * 11/1998 Some et al. ................. 250/584
6,614,873 B1 * 9/2003 Taylor et al. .................. 378/62

FOREIGN PATENT DOCUMENTS

| JP | 63-253348 | 10/1988 |
|----|-----------|---------|
| JP | 01-227139 | 9/1989 |
| JP | 04-123173 | 4/1992 |
| JP | 04-155581 | 5/1992 |
| JP | 217807 | 8/2000 |

* cited by examiner

*Primary Examiner*—Daniel Miriam
*Assistant Examiner*—Seyed Azarian
(74) *Attorney, Agent, or Firm*—Sughrue Mion, PLLC

(57) ABSTRACT

The image information processing system includes a radiation image generating device for generating a radiation image, an image information processing device having a function of inputting patient information, a function of receiving the radiation image and a function of performing predetermined image processing on the received radiation image, an external memory device for temporarily storing at least one of the radiation image and the processed radiation image in relation to the patient information and an image display device for displaying at least one of the radiation image and the processed radiation image. The image information processing device has a function for making a copy of capture items which include at least the patient information and capture information relevant to the radiation image when there is an indication that the radiation image is a damaged picture.

9 Claims, 2 Drawing Sheets though recorded as image data; an identification information recording device for registering identification information pertaining to the patient; and an image recording device for recording in relation to the registered identification information pertaining to the patient the radiation image as a visible image on a recording material such as a photographic photo-sensitive material based on the image data that has been obtained.

IMAGE INFORMATION PROCESSING SYSTEM

BACKGROUND OF THE INVENTION

1. Field of the Invention

The present invention relates to an image information processing system for generating radiation image information from a patient at a hospital, for example, and reading the radiation image information from a stimulable phosphor sheet or the like which has recorded the above radiation image information, or, directly generating the radiation image information using a solid state sensor and performing image processing on the thus generated radiation image information, and particularly, to an image information processing system for receiving radiation image information generated by a radiation image generation device such as a radiation image reading device, performing the predetermined image processing on the received radiation image information, and then outputting the processed radiation image information to an image outputting device in association with patient information.

2. Description of the Related Art

At present, there is used a system for recording and reproducing radiation image information utilizing a stimulable phosphor which, when exposed to radiation (i.e., X-rays, α-rays, β-rays, γ-rays, electronic beams, ultra-violet rays, etc.), stores a portion of that radiation energy and then, when exposed to stimulating rays such as laser light, visible light or the like, produces photostimulated luminescence corresponding to the stored energy.

An radiation image information processing system has been proposed and made practical in JP 63-253348 A, JP 1-227139 A, JP 4-123173 A and JP 4-155581 A by the present assignee as examples of this type of radiation image information recording and reproducing system. Such system includes a radiation image reading device for scanning with a laser or other such stimulating rays a stimulable phosphor sheet on which the radiation image information of the patient is temporarily stored and recorded by photographing a patient at a hospital, for example, by means of an X-ray image capturing device or the like, to generate a photostimulated luminescence, and photoelectrically reading the photostimulated luminescence obtained to produce image data; an identification information recording device for registering identification information pertaining to the patient; and an image recording device for recording in relation to the registered identification information pertaining to the patient the radiation image as a visible image on a recording material such as a photographic photo-sensitive material based on the image data that has been obtained.

In this conventional type, of radiation image information processing system, before the image of the patient is captured, or at the time when the image is captured, identification (ID) information containing patient information such as the name, sex, date of birth and identification (ID) number and capturing information regarding the taking of the image, such as the date when the image was taken, the region that was taken, the method by which the image was taken and bar code information regarding the stimulable phosphor sheet onto which the image was captured are registered in the identification information recording device (i.e., ID terminal) which is disposed close to the radiation image capturing device and the like. On the other hand, the ID terminal sends to the radiation image information reading device such information as the registered identification information, conditions for the processing of the radiation image which has been read with the radiation image information reading device, information pertaining to the destination to which the processed radiation image is to be outputted (i.e., the destination to which the image data is delivered) conditions for the outputting of the process radiation image at the image recording device, and also, the destination to which the outputted radiation image is to be distributed, such as an internal medicine department or surgery department of a hospital, for example, or other such dispensary departments or clinics.

Then, at the radiation image information reading device, a bar code which is on the back side of the stimulable phosphor sheet is read and this bar code is associated with the patient ID information obtained from the ID terminal, and also, the radiation image information which has been captured is read from the stimulable phosphor sheet, the image processing and other such processing are performed in accordance with the processing conditions which have been obtained, and the processed radiation image which has been thus obtained is sent to the image recording device together with the output conditions. At the image recording device, the processed radiation image is outputted as a hard copy image such as a permeable film image being equivalent to an X-ray film image or reflected paper image based on the obtained output conditions. The outputted radiation image is distributed by a well-known means to a distributing destination obtained from the ID terminal.

In other words, in the conventional radiation image information processing system disclosed in the above-mentioned publications, the radiation image information reading device is capable of reading vast quantities of the stimulable phosphor sheet, and because of decreased costs it is possible to use more than one radiation image information reading device, and therefore, even if it is connected to one or to a plurality of radiation image information reading devices and a plurality of ID terminals, and the ID terminal is made so that it can be arranged close to not only the device for capturing the radiation image but also close to a reception desk or such of the hospital, the dispensary departments or clinics, or such so that the input of the patient information and the cross-check of the stimulable phosphor sheet against the patient information at the image capturing device is made easy and efficient, and, no matter which ID terminal registered the stimulable phosphor sheet, it is still possible for a freely chosen radiation image information reading device to read this and it is possible to achieve efficient operation of the radiation image information reading devices.

Incidentally, in the capturing of the radiation image it is possible for failures (referred to as "picture damage") to occur due to various causes. For example, in cases ranging from simple cases such as the case when the patient, who is the subject to be photographed, moves inadvertently, to cases such as the case of a setup miss in which the conditions for the taking of the image (ex, the quantity of X-rays or the like) are set inappropriately, picture damage can result due to the various causes.

These types of picture damage are discovered not at the time of the taking of the image, but at a point after a duration of time has elapsed (specifically, when the doctor makes a diagnosis, or inspects the images), and therefore, in order to correct the problems and retake the image it is first necessary to know how the conditions for taking the image are configured in the beginning. However, conventionally, in the case where this type of picture damage occurs the damaged picture image itself and the conditions of the image taking are destroyed, so there is the problem that when the image is to be retaken (retaking of the image is abbreviated as "retaking") it is necessary to input the conditions for the taking of the image all over again.

One reason why this problem arises is because the time of the taking of the image and the time when the taken image is used (which is mentioned above as the time when the doctor makes the diagnosis or inspects the image) are different times, and so the picture damage is only discovered after a certain amount of time from the taking of the image has elapsed, and even if this is not the case the problem would still arise because when the image is judged to be damaged, the damaged picture image is destroyed together with the conditions for the taking of the image.

SUMMARY OF THE INVENTION

The present invention has been developed in light of the above issues, and so it has as an object to resolve the problems in the conventional art and provide an image information processing system in which it is easy to input the image capturing conditions for the retaking of the image in the case where picture damage has occurred.

In order to attain the object described above, the present invention provides an image information processing system comprising: a radiation image generating device for generating a radiation image; an image information processing device having a function of inputting patient information, and a function of receiving the radiation image generated by the radiation image generating device and performing predetermined image processing on the received radiation image; an external memory device connected to the image information processing device, for temporarily storing at least one of the radiation image received from the radiation image generating device and a processed radiation image on which the predetermined image processing has been performed by the image information processing device in relation to the patient information; and an image display device connected to the image information processing device, for displaying at least one of the radiation image and the processed radiation image; wherein the image information processing device has a function for, in case of an indication that the radiation image is a damaged picture, making a copy of capture items which include at least the patient information and capture information relevant to the radiation image.

Preferably, the image display device displays at least one of the radiation image and the processed radiation image in relation to the capture items.

Preferably, the image information processing device stores the copy of the capture items in relation to at least one of the radiation image and the processed radiation image.

Preferably, the copy of the capture items and at least one of the radiation image and the processed radiation image are stored in an image information storing device external to the image information processing system.

DETAILED DESCRIPTION OF THE PREFERRED EMBODIMENTS

Hereinafter, detailed explanation will be made of an embodiment of the present invention, based on the attached drawings. Note that in the subsequent explanation, an example is given of the most simple embodiment of the present invention, that is, an image information processing system comprises an "image and information processing device" (referred to hereinafter as an "IIP"), one radiation image reading device and one image storage device which are connected thereto and one radiation image capturing device. The IIP has one image information processing device, one image display device, one image recording device and one external recording device. However, it goes without saying that the number of the respective devices which are component elements of the invention may be freely determined.

Further, in the subsequent explanation, for the radiation image generating device for generating the radiation image of the patient, for example, a typical example is used of a radiation image reading device for reading the radiation image of the patient or the like which has been captured temporarily on the stimulable phosphor sheet by means for the radiation image capturing device. However, the present invention is not limited to this, and it goes without saying that in the radiation image capturing device, for example, in place of the X-ray film or the stimulable phosphor sheet it is possible to use a type of radiation image generating device which includes an array of a large number of solid state sensors and directly generates the radiation image (i.e., data) of the patient or such.

Figure 1:
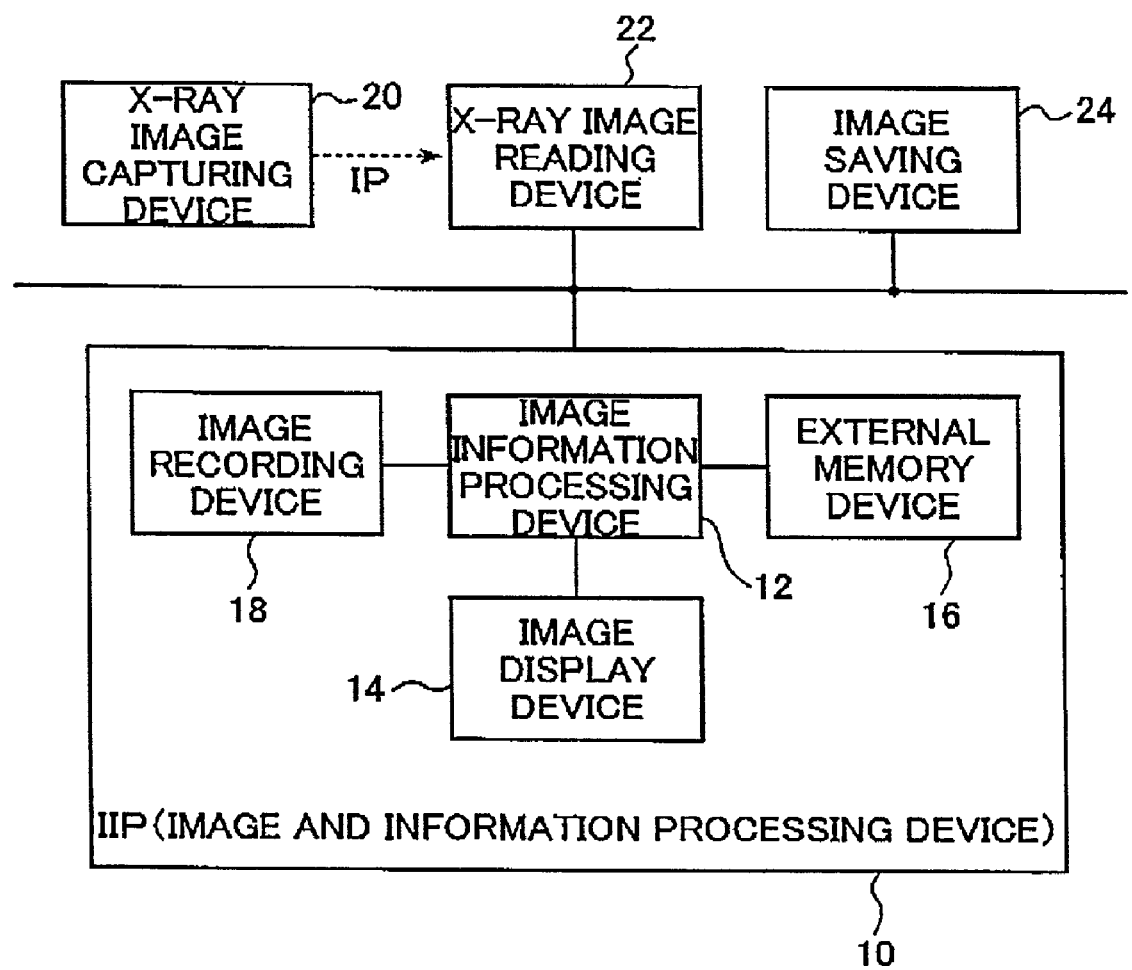
FIG. 1 is a diagram illustrating a construction of an IIP (image and information processing device) according to an embodiment of the present invention.

FIG. 1 is a diagram depicting a construction of an image information processing system including the IIP (image and information processing device) 10 according to the present embodiment constructed as described above. In the figure, reference numeral 12 is an image information processing device, 14 is an image display device, 16 is an external storage device, 18 is an image recording device, 20 is an X-ray image capturing device for use as the radiation image capturing device, 22 is an X-ray image reading device for use as the radiation image reading device, and 24 is an image saving device.

In the system according to the present embodiment, the X-ray image reading device 22, as recited in the above-mentioned publications JP 63-253348 A and JP 4-155581 A, is a device for irradiating the stimulating rays onto the stimulable phosphor sheet onto which the predetermined region of the patient is captured at the X-ray image capturing device 20 or other such image capturing device, and photo-electrically reading the stored and recorded X-ray images of the patient as image data. Note that the X-ray image reading device 22 used in the present embodiment is different from the image reading device disclosed in the above publications, and it has a function of sending to the image information processing device 12 in the IIP 10, which is a specific image information processing device being configured in advance, the unprocessed X-ray images which have not yet been subjected to the image processing for outputting the read X-ray images in an appropriate manner to the image recording device and the image display device, or the image processing in accordance with the image processing conditions that have been configured in advance.

Note that at the X-ray image capturing device 20, when the image of the predetermined region of the patient is to be captured, the bar code recorded on the back side of the stimulable phosphor sheet is read and related to identification (ID) information such as the identification (ID) number of the patient or the like. Therefore, in the image information reading device 22, when the X-ray image of the patient is to be read from the stimulable phosphor sheet (i.e., "imaging plate", or "IP"), the bar code on the back side of the stimulable phosphor sheet is read in the same way, and the identification information such as the ID number of the patient or the like which is related to at the X-ray image capturing device 20 can be cross-checked. This relating, however, may be omitted in cases such as that of the present embodiment, in which the X-ray image reading device 22 and the IIP 10 are connected to each other one-to-one.

The image information processing device 12 is the most characteristic portion of the present invention, and it is provided with a function for serving as a so-called ID terminal which inputs the patient ID information which includes the patient information or the patient information and the image capturing information; a function of receiving the unprocessed radiation image which has not yet been subjected to the image processing and which has been read out from the X-ray image reading device 22; a function of performing appropriate image processing to prepare the image for outputting, or else performing image processing in accordance with image processing conditions that have been configured in advance in the image capturing information, on the unprocessed X-ray image which has not yet been subjected to the image processing and which has been received from the X-ray image reading device 22; and a function for sending the processed X-ray image on which the image processing has been performed, to at least one of two distribution destinations which are an external memory device 16 and an image saving device 24.

Further, it is desirable for the image information processing device 12 to have a function for making the external memory device 16 store at least the inputted patient information in such a way so as to be searchable, searching the external memory device 16 the next time by using a part of the patient information as a search key word, and reading out from the patient information stored in the external memory device 16 that patient information which falls under the key word. In the case where there has been a change made to the patient information, this should be updated and recorded in the external memory device 16. By configuring a construction such as this, it becomes possible to make the input operations of patient information more efficient and lighten the load on the operator.

Here, the external memory device 16 is a temporary storage device having a function for temporarily storing either one of or both the X-ray image which has not yet been subjected to image processing and which was received from the X-ray image reading device 22 and the X-ray image which has been subjected to the image processing by means of the image information processing device 12, in relation to the patient ID information including the patient information and the image capturing information which are inputted into the image information processing device 12, that is to say, by establishing the relationship or the correspondence either one of or both the unprocessed X-ray image and the processed X-ray image, and the patient ID information.

Note that it is preferable for there to be many X-ray images being stored temporarily in the external memory device 16, and it is also preferable for them to be stored for a long period of time; however, these are not particular restrictions on the present invention, and can be selected as appropriate in accordance with storage capacity, costs, and the size of the hospital, or the health consultation center, health screening center or the like for wellness examination where the present processing device (i.e., the IIP) 10 is to be used.

The image display device 14 is for displaying the ID information such as the patient information and the image capturing information which has been inputted by the operator into the image information processing device 12 and registered, for purposes of confirmation at the time when they are inputted or after they are inputted, and further, displaying either one of or both the unprocessed X-ray image received from the X-ray image reading device 22 and the processed X-ray image by means of the image information processing device 12, in relation to or in correspondence with the identification (ID) information mentioned above, or displaying with a part of or all of the ID information The image display device 14 which is to be used in the present invention is not particularly limited, and so a CRT display device (i.e., monitor), LCD (monitor), plasma display device or other such well-known display device or monitor may be used.

The operator inputs the ID information which includes the patient information such as the patient's name, sex, date of birth and ID number, for example, into the image information processing device 12, and this is registered there. Note that the image information processing device 12 can issue to the patient a magnetic card onto which the patient's information has been inputted, or the patient information can be read from the magnetic card (i.e., a special purpose magnetic card or a consultation ticket) issued to the patient in advance by this image information processing device 12, by another processing device, or at the reception desk or other such location in the hospital, for example. Further, at the same time, it is also possible for the operator to input, for example, the month and date that the image was taken, the region taken, the method by which the image was captured, the bar code information of the stimulable phosphor sheet onto which the image was captured, the image processing conditions and other such image capturing information, as ID information and register the information. By doing this, the patient information, the image capturing information and other such information (referred to hereinafter generally as the image capture items) are displayed on a monitor of the image display device 14 connected to the image information processing device 12.

Further, the above-mentioned image recording device 18 uses the image data signal of the already processed X-ray image which has been sent from the image information processing device 12 and outputs a hard copy image bearing the X-ray image which is to be provided for the medical diagnosis, in correspondence with the patient's ID information or with a part of this. The image recording device which is used here is not necessarily limited, but it is desirable that it can record and output a hard copy image having capacity which is equivalent to the X-ray film image provided for the medical diagnosis.

Typical examples of this kind of image recording device include ones in which a photographic photo-sensitive material (such as photo-sensitive film) is scanned and exposed by means of a modulated light beam of laser beam or the like which has been modulated in response to an image data signal of the X-ray image received from the image information processing device 12, a latent image therein is recorded, the exposed photo-sensitive material is developed by means of developing processing and the X-ray image is outputted as a hard copy image; and also includes ones in which an image is recorded onto heat-sensitive material (such as thermal film) by means of a thermal recording head (i.e., thermal head) which is modulated in response to the image data signal of the X-ray image, or by means of a heat mode laser which is modulated in the same way, and thus the output is then performed.

Note that the photo-sensitive material and heat-sensitive material to be used in the image recording are not particularly limited, and photosensitive film and thermal film are desirable. Examples of the material include materials which are capable of wet developing or dry developing, such as silver salt photographic photo-sensitive materials, photo-sensitive thermal developing materials, various heat-sensitive materials, and other such well-known photo-sensitive and heat-sensitive materials.

Additionally, it is also possible to use another well-known image recording device, such as an image recording device which uses an electrophotography using photo-sensitive bodies and toner to transfer to image receiving materials, or an image recording device which uses a format in which the image is transferred to image recording materials by means of a sublimation (ablation) method.

Next, the image saving device 24 is a device for storing at least one of the image data signal of the already processed X-ray image which has been sent from the image information processing device 12 and the image data signal of the unprocessed X-ray image long-term by establishing relationship or correspondences between at least one of the above image data signals and the patient's ID information, and saving it as an X-ray image database. The capacity of the image saving device 24 (i.e., the database capacity) is not particularly restricted, and can be selected as appropriate in accordance with the size of the present processing device (i.e., the IIP) 10.

Note that the storage of the X-ray image data in the image saving device 24 can be performed at any time. That is, if it is to have a back up function, then it is preferable to storing the X-ray image data at the same time as when this data is temporarily saved to the external memory device 16; however, considering the issue of memory capacity, the data should be stored when it is deleted from the external memory device 16. Further, the types of radiation images which are to be saved in the image saving device 24 as the database are not particularly limited, and it is possible to save all of the radiation images which are temporarily stored in the external memory device 16, but it is also possible to select a portion thereof and save only this portion. It is also possible to perform the selection for the radiation images to be saved into the image saving device 24 at the time when the temporarily stored radiation images are deleted from the external memory device 16.

The ID information inputting function of the image information processing device 12 can be realized by means of a keyboard or a mouse for performing inputting and monitor, for example, and is a function for inputting and confirming or cross-checking the patient information, image capturing information, and the like. Further, image information processing device 12 also has a function for, in the case where the inputted patient information, image capturing information, etc. (i.e., the capture items) are stored in the external memory device 16 as mentioned above, searching the external memory device 16 and cross-checking and confirming a part or all of the capture items, or obtaining, searching for, cross-checking and confirming a part or all of the patient's ID information by means of the magnetic card issued to the patient.

The IIP 10 according to the present embodiment is basically constructed as described above, but explanation will be made hereinafter regarding its operations, according to the operation flow chart depicted in FIG. 2.

Figure 2:
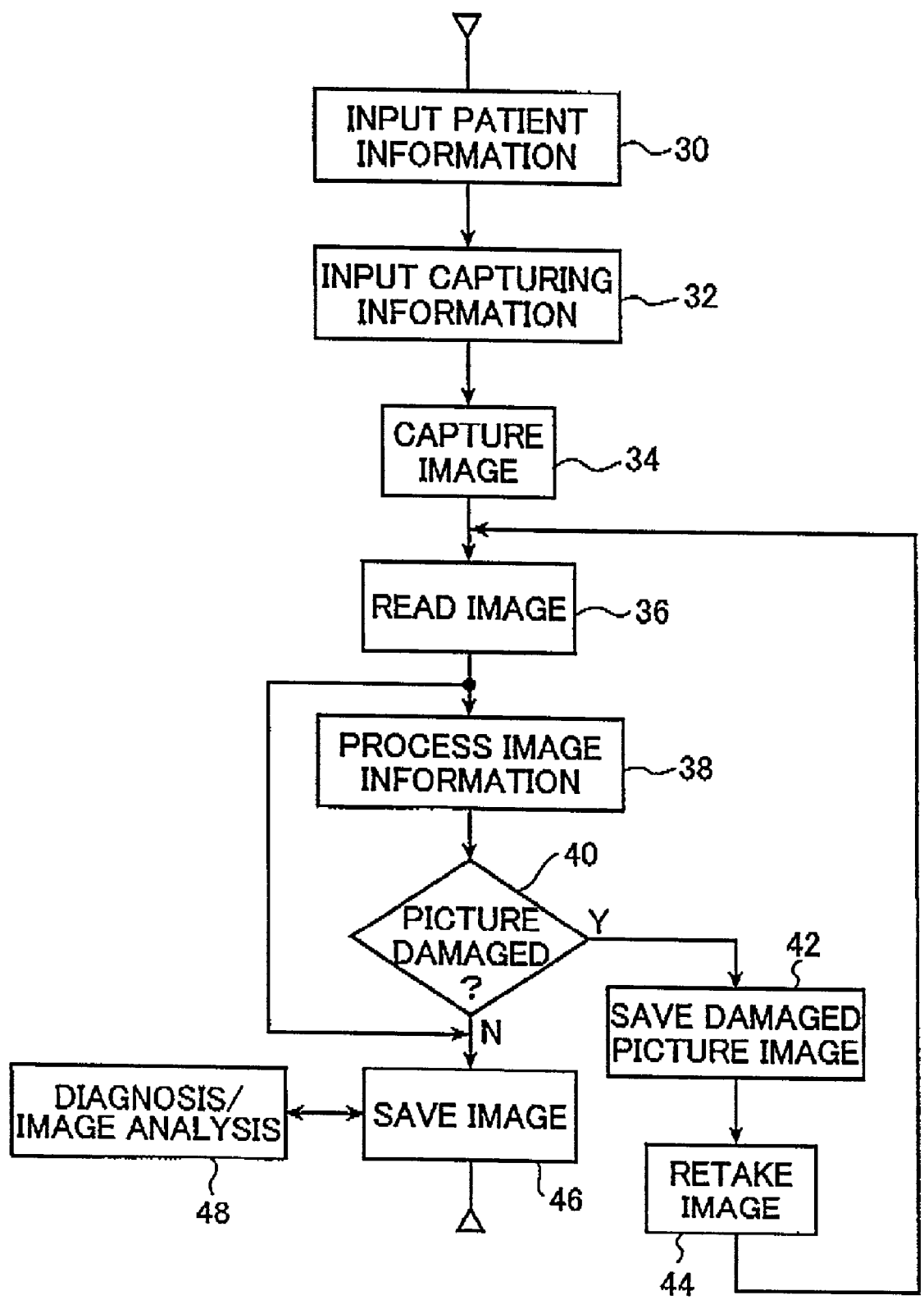
FIG. 2 is a flow chart illustrating a summary of operations of the IIP depicted in FIG. 1.

As shown in FIG. 2, the operations of the IIP 10 according to the present embodiment include, in outline, the steps of inputting the patient's information and the capturing information (steps 30 and 32), executing the capturing of the image based on these sets of information (step 34), reading the captured image (step 36), performing the predetermined image processing on the image which has been read out (step 38), judging or determining the quality of the results of the capture (i.e., the image processing results) (step 40), saving the damaged picture image and retaking the image in the case where the quality is judged or determined to be not good (steps 42 and 44), saving the image in the case where the quality is judged to be good, (step 46) and using this image for the diagnosis by the doctor (step 48). More detailed explanation will be made hereinafter.

In the IIP 10 depicted in FIG. 1 the patient information such as the patient's name, sex, date of birth, ID number and the like, for example, are inputted, and this is registered in the image information processing device 12. These sets of information may be inputted by forwarding them from an outside of the device to the image information processing device 12. However, it is also possible to use the input function of the image information processing device 12. Further, as mentioned above, it is also possible for a part of the patient information to be used as a search term to search the external memory device 16, and for the corresponding patient information which falls under the term to be acquired. Accordingly, it is possible to make the process of inputting the patient information more efficient and lighten the load on the operator, for example.

Next, in the X-ray image capturing device 20 the image capture of the predetermined region of the patient is performed according to the capture information, such as the date of the image capture, the region taken, the method by which the image is to be captured and other such information having been registered in a fashion similar to the patient information, and this X-ray image is stored and recorded on the above-mentioned stimulable phosphor sheet. At this time, it is possible, when necessary, to read the bar code on the back side of the stimulable phosphor sheet, to register it as capture information, and to establish a relationship or a correspondence between this bar code and the patient's ID information, such as the ID number and other such patient information, for example.

In this way, the stimulable phosphor sheet on which the X-ray image of the predetermined region of the patient has been stored and recorded is loaded into the X-ray image reading device 22 and the X-ray image is read. Note that at this time, as described above, the bar code on the back side of the stimulable phosphor sheet is read, and based on this bar code, the relationship or the correspondence can be established between the X-ray image and the capture items mentioned above, which include the patient information such as the patient's ID code and the capture information.

According to what is described above, the X-ray image that is read out at the X-ray image reading device 22 is sent together with the above-mentioned capture items to the image information processing device 12. In the image information processing device 12, the image processing is performed on this X-ray image which has thus been received and this is displayed on the image display device 14 for confirmation, and after that, the relationship or the correspondence is established between the processed X-ray image and the capture items, and the processed X-ray image is temporarily stored in the external memory device 16 in relation to the capture items. Note that it is also possible to send from the image information processing device 12 to an image output device such as an image recording device 18, for example, for output to be performed.

In the image which has been subjected to the image processing by means of the image information processing device 12, before the image is used, a quality judgment is performed on this image by comparing against the capture items. Here, if a blatant disadvantage is discovered then the image is judged to be a damaged picture image and the image is saved as a damaged picture image and forwarded to be retaken. Of course, it goes without saying that a judgment is performed in a similar fashion on the image that is retaken.

On the other hand, when the result of the quality judgment indicates the processed X-ray image to be good, then a relationship or a correspondence is established between the processed image (and, as necessary, the unprocessed X-ray image) and the above-mentioned capture items and stored long-term in the image saving device 24 to be saved as radiation image database. Good images stored in the image saving device 24 are used by the doctor for diagnosis of the patient and image analysis.

In the procedure steps above, a characteristic procedure of the IIP 10 according to the present embodiment is that it is configured so as not to destroy any image, but to establish the correspondence between the image and the capture items and save the image even in the case where the processed X-ray image is judged to be a damaged picture image, and this enables the input of the capture items to be performed significantly more efficiently when the image is to be retaken, as described hereinafter.

That is, if the purpose for retaking the image is because the subject moved inadvertently then there is no need to change the capture items which can remain as they were the previous time, so it is possible to retake the image right away without further manipulations. Further, even in the case where it is necessary to alter the capturing conditions in some way, then just that part is corrected and it is possible to re-take the image right away.

According to the above embodiment, even in the case where an X-ray image which has been captured from a patient is judged to be a damaged picture, the capture items for that image are still saved together with that image, so an obviously practical effect can be obtained such that it is possible to retake the image by making only a minute correction of cross-checking the capture items and altering a part of the capturing conditions as necessary, for example.

Note that the above embodiment illustrated one example of the present invention, the present invention is not limited to this embodiment, and, of course, various improvements and alterations may be made within the scope of the present invention without departing from its spirit.

For example, the above embodiment is the most simple embodiment of the present invention, in which an example is given of an image information processing system in which the IIP, including one image information processing device, one image display device, one image recording device and one external memory device, is connected to one radiation image capturing device, one radiation image reading device and one image saving device; however, the quantity of each of the constituent devices may be determined freely, as stated above.

Specifically, an image information processing system may also be used quite well which has a plural number of the IIPs having the construction described above, and being connected through a network to one or more radiation image capturing devices, radiation image reading devices, image storing devices, etc. In this case, as described above, between the radiation image capturing device, the radiation image reading device and the IIP it is possible to use the bar code on the back side of the stimulable phosphor sheet to establish the correspondences between the image information pertaining to the stimulable phosphor sheet and the patient's ID information, such as the patient information ID number and the like.

Further, the above-mentioned embodiment gave an example in which a radiation image reading device for reading the radiation image information from the stimulable phosphor sheet on which the radiation image information was recorded, is used as a radiation image generating device; however, the present invention is not limited to this configuration, and any type of radiation image generating device capable of generating radiation images may be used. For example, it is also possible to use the radiation image capturing device disclosed in JP 2000-217807 A by the present applicant, which uses a radiation detection cassette comprising a radiation solid state sensor for sensing a radiation image and an image memory for storing image data outputted from this radiation solid state sensor, is used as a radiation image generating device.

As is explained in detail above, according to the present invention, an effect is obtained such that an image information processing system is realized in which the input of the capturing conditions for the retaking of the image in the case where a damaged picture image is generated is made easy.

That is, according to the present invention, in the case where a damaged picture image is generated, the relationship or the correspondence is established between the damaged picture image and the capture items, and the damaged picture image is saved in relation to the capture items so that cross-checking can be performed. By this construction, an extremely practical effect is obtained such that the input of the capture items at the time of the retaking of a damaged picture image is made to be significantly more efficient.

What is claimed is:

1. An image information processing system comprising:
   a radiation image generating device for generating a radiation image;
   an image information processing device having a function of inputting patient information, and a function of receiving said radiation image generated by said radiation image generating device and performing predetermined image processing on the received radiation image;
   an external memory device connected to said image information processing device, for temporarily storing at least one of said radiation image received from said radiation image generating device and a processed radiation image on which said predetermined image processing has been performed by said image information processing device in relation to said patient information; and
   an image display device connected to said image information processing device, for displaying at least one of said radiation image and said processed radiation image; wherein
   said image information processing device has a function for, in case of an indication that said radiation image is a damaged picture, making a copy of capture items which include at least said patient information and capture information relevant to said radiation image.

2. The image processing system according to claim 1, wherein said image display device displays at least one of said radiation image and said processed radiation image in relation to said capture items.

3. The image processing system according to claim 1 wherein said image information processing device stores said copy of the capture items in relation to at least one of said radiation image and said processed radiation image.

4. The image processing system according to claim 1, wherein said copy of the capture items and at least one of said radiation image and said processed radiation image are stored in an image information storing device external to said image information processing system.

5. The image processing system according to claim 1, wherein the external memory device stores both said radiation image received from said radiation image generating device and said processed radiation image.

6. The image processing system according to claim 1, wherein the capture items are used as image capturing conditions for processing a second radiation image.

7. The image processing system according to claim 1, wherein the damaged picture comprises an image of a patient that moved during exposure of the image.

8. The image processing system according to claim 1, wherein the damaged picture comprises an image of a patient that was exposed with improper set up conditions.

9. The image processing system according to claim 1, wherein the capture items are used as image capturing conditions for retaking a second image.

* * * * *